United States Patent [19]

Resch

[11] Patent Number: 4,705,793

[45] Date of Patent: Nov. 10, 1987

[54] PYRAZOLO[3,4-B]PYRROLO[3,4-E]PYRI-DINE-5(1H)-ONE AND 1-H-PYRAZOLO[3,4-B][1,6]NAPHTHYRI-DINE-5(6H)-ONE DERIVATIONS, USEFUL AS ANTI-ANXIETY AGENTS

[75] Inventor: James F. Resch, Wilmington, Del.

[73] Assignee: ICI Americas Inc., Wilmington, Del.

[21] Appl. No.: 749,142

[22] Filed: Jun. 25, 1985

[30] Foreign Application Priority Data

Aug. 20, 1984 [GB] United Kingdom ............... 8421116

[51] Int. Cl.$^4$ .................. A61K 31/395; C07D 471/14
[52] U.S. Cl. ...................................... 514/293; 546/82
[58] Field of Search ........................... 546/82; 514/293

[56] References Cited

U.S. PATENT DOCUMENTS 4,563,525  1/1986  Campbell ............................. 546/82

FOREIGN PATENT DOCUMENTS 0094175  1/1983  European Pat. Off. ............. 546/82

OTHER PUBLICATIONS

March, J. Adv. Org. Chem. 2nd ed., pp. 377–378, 935, 807.

Primary Examiner—Henry R. Jiles
Assistant Examiner—J. Richter
Attorney, Agent, or Firm—Rosemary M. Miano

[57] ABSTRACT

Novel pyrazolo[3,4-b]pyridine lactams which are useful as anxiolytics are disclosed including methods of preparation, pharmaceutical compositions containing them and intermediates used in their preparation.

6 Claims, No Drawings

PYRAZOLO[3,4-B]PYRROLO[3,4-E]PYRIDINE-5(1H)-ONE AND 1-H-PYRAZOLO[3,4-B][1,6]NAPHTHYRIDINE-5(6H)-ONE DERIVATIONS, USEFUL AS ANTI-ANXIETY AGENTS

BACKGROUND OF THE INVENTION

The present invention relates to pyrazolo-[3,4-b]-pyridine lactams which are useful as anxiolytic agents, methods for their preparation, pharmaceutical compositions containing them and intermediates used in their preparation.

In European Patent Publication No. 0094175 (see U.S. Pat. No. 4,511,568 to Bare et al.) there are described anxiolytic tricyclic derivatives of the formula I:

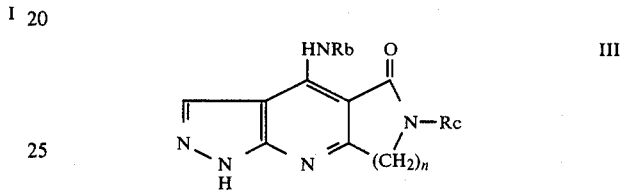

in which $R^1$ is, inter alia, alkynyl of 3 to 10 carbon atoms. However, there is no mention therein of any specific alkynyl radical as a value for $R^1$, nor there any exemplified compound in which $R^1$ is an alkynyl radical. It has now been discovered, and herein lies our invention, that compounds of the formula I in which $R^1$ is a pent-3-ynyl or hex-4-ynyl radical are at least four times as potent as anxiolytic agents as the corresponding compounds which carry an n-pentyl or nhexyl radical in the same position.

SUMMARY OF THE INVENTION

The compounds of the invention are pyrazolo[[3,4-b]pyridine lactams having a selected alkynyl substitution at the "1" position.

DETAILED DESCRIPTION OF THE INVENTION

According to the invention there is provided an alkynyl derivative of the formula II:

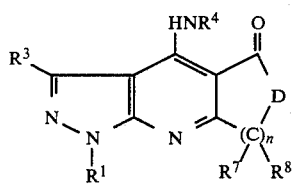

in which
Ra is pent-3-ynyl or hex-4-ynyl;
Rb is hydrogen or (1-10C)alkanoyl:
Rc is (1-6C)alkyl, (3-6C)alkenyl, or (3-6C)alkynyl: and
n is 1 or 2:
and the pharmaceutically-acceptable acid-addition salts thereof.

A particular value for Rb is acetyl, propionyl, butyryl, valeryl, or hexanoyl.

A particular value for Rc is ethyl, n-propyl, n-butyl, 2-propenyl, 2-propynyl, or 2-butynyl.

A particular acid-addition salt is one formed with hydrochloric, hydrobromic, sulphuric, nitric or phosphoric acid.

Preferred compounds of the invention are those of formula II in which (a) Ra is a pent-3-ynyl, Rb is hydrogen, Rc is n-propyl and n is 1: (b) Ra is pent-3-ynyl, Rb is hydrogen, Rc is 2-propenyl and n is 1; and (c) Ra is pent-3-ynyl, Rb is propionyl, Rc is propyl, and n is 1.

The compounds of formula II may be prepared by using methods known in part for the preparation of chemically similar compounds. Thus the following processes are provided as a further feature of the invention, Ra, Rb, Rc and n having the meani.ngs stated above unless indicated otherwise.

(a) alkynylation of a compound of the formula III:

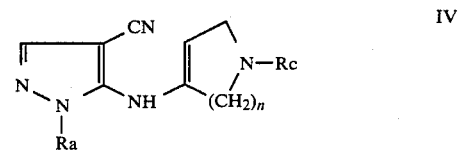

or tautomers thereof:

(b) for those compounds in which Rb is hydrogen, cyclization of a compound of the formula IV:

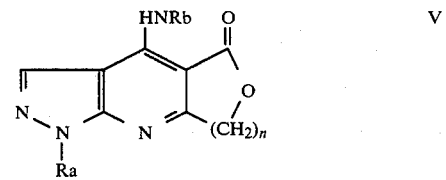

(c) for those compounds in which Rb is alkanoyl, acylation of a compound of the formula II in which Rb is hydrogen.

(d) reaction of a compound of the formula V:

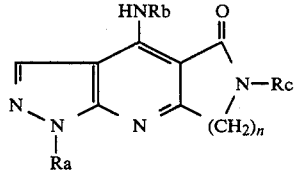

with an amine of the formula Rc-NH₂.

(e) for those compounds in which Rb is hydrogen, cyclization of a compound of the formula VI:

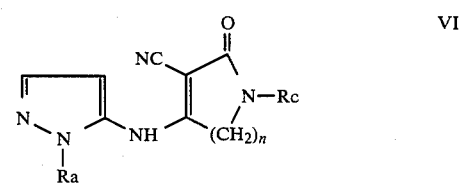

(f) reaction of a compound of the formula VII:

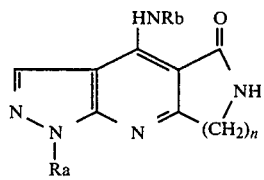

with an alkylating, alkenylating, or alkynylating agent.

Process (a) is the preferred method. The starting material of formula III for process (a) in which Rb is hydrogen may be prepared by the method described for the preparation of the starting materials in, for example, Examples 1, 4, and 10. In method (a) it is preferred to use a chloroethyl protecting group to form the base pyrazolo [3,4-b]pyridine lactam before the selected alkynyl is added as Ra to the "1" position. Thus for method (a) a compound of formula VIII:

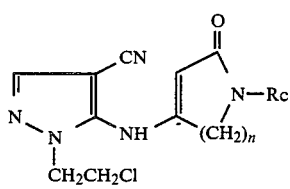

may be cyclized to a compound of formula IX:

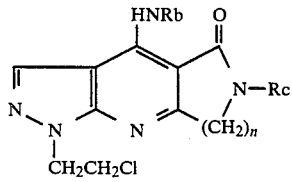

Dehydrohalogenation with removal of HCl gives an alkene of formula X:

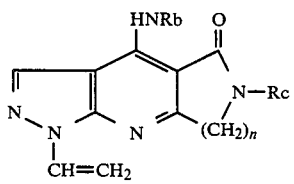

and hydrolysis provides a compound of formula III. Alkynylation according to method (a) may then be performed. Use of this method with the chloroethyl protecting group is especially desirable when Rb is hydrogen and Rc is propyl or 2-propenyl.

The starting material of the formula IV for use in process (b) may be prepared by the method described for the preparation of the starting material in Example 3. In method (b), for example, 5-amino-4-cyanopyrazole may be mixed under appropriate conditions with RaX, where X is a halogen selected from the group consisting of fluoro, shloro, bromo and iodo to form a compound of formula XI:

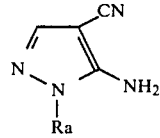

The compound of formula XI may then be mixed under appropriate conditions with a pyrrolidinone of formula XII:

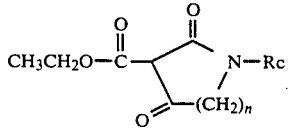

or tautomers thereof to give a compound of formula IV.

Pharmaceutically acceptable acid addition salts may be formed by reacting a compound of formula II with an appropriate acid, e.g., by dissolving a compound of fomula II, adding a selected acid to the solution and recovering the salt.

As indicated above, the compounds of the present invention are at least four times as potent as anxiolytic agents as the corresponding compounds from European Patent Publication 0094175 which carry an n-pentyl or n-hexyl radical in place of Ra. This difference of potency may be demonstrated in the Shock-Induced Suppression of Drinking (Rats) Test (SSD) described in *Pharmacology Biochemistry and Behaviour,* 1980, Vol. 12, pages 819–821. This test may be carried out as follows:

Male rats in the weight range of 200 to 220 g. are deprived of water for 48 hours and deprived of food for 24 hours before testing. Normally, the rats are orally intubated and receive a volume of 5 ml./kg. containing the appropriate concentration of test compound (based on mg./kg. body weight). The vehicle control group of rats is also intubated by mouth. A positive control group of rats is also orally administered a control dose of 18 mg./kg. of chlordiazepoxide. Random selection of the rats is utilized in dosing. The rats are returned to the cage for one hour. Sixty minutes after drug administration, the rat is quietly removed from its cage and the hind feet wiped with Signa electrode gel made by Parker Laboratories of Orange, New Jersey. When intraperitoneal (i.p.) administration is used, the protocol is identical except that the drugs are administered in varying concentrations in a volume of 5 ml./kg. 30 minutes prior to testing. Concentrations ranged from 0.4 to 50 mg./kg. The rat is placed on the floor in the chamber facing the licking tube. The animal is allowed 5 minutes to make 20 licking responses and receive the first shock (0.5 mA). If this response does not occur, the animal is removed and eliminated from the study. If 20 licking responses are made, the animal is permitted an additional 3 minutes during which time each Z0th lick is paired with a 0.5 mA shock. This period is automatically started, counted and terminated. The number of licks and shocks are recorded. The activity of the compound tested is evaluated by comparing the mean shocks of the group dosed with the test compound to both the mean shocks of the vehicle and positive control groups via a Students' t-test. In general, an increase in the number of shocks received compared to the control is indicative of the anti-conflict or anti-anxiety activity of the compound.

In the SSD test the most preferred compound of the invention, that of the formula II in which Ra is pent-3-ynyl, Rb is hydrogen, Rc is n-propyl and n is 1, when dosed by the oral route, is at least fifteen times as potent as the corresponding compound from European Patent Publication No. 0094175 in which Ra is n-pentyl.

According to a further feature of the invention there is provided a pharmaceutical composition which comprises an alkynyl derivative of the invention in association with a pharmaceutically-acceptable diluent or carrier.

The pharmaceutical composition may, for example, be in a form suitable for oral, rectal or parenteral administration, for which purposes it may be formulated by means known to the art into the form of, for example, tablets, capsules, aqueous or oily solutions or suspensions, emulsions, dispersible powders, suppositories or sterile injectable aqueous or oily solutions or suspensions.

A preferred pharmaceutical composition of the invention is one suitable for oral administration in unit dosage form, for example a tablet or capsule which contains between 0.1 mg. and 500 mg. of the alkynyl derivative, or one suitable for intravenous, intramuscular or subcutaneous injection: for example, a sterile injectable containing between 0.1% and 10% w/w of the alkynyl derivative.

The pharmaceutical composition of the invention will normally be administered to mammals such as man for relief of anxiety and tension in the same manner as that employed for chlordiazepoxide, due allowance being made in terms of dose levels for the potency and duration of actions of the alkynyl derivative of the invention relative to chlordiazepoxide. Thus each individual, will receive an oral dose of between 0.5 mg. and 500 mg., and preferably between 0.5 mg. and 20 mg., of alkynyl derivative, or an intravenous, subcutaneous or intramuscular dose of between 0.5 mg. and 100 mg., and preferably between 0.5 mg. and 20 mg., of the alkynyl derivative, the composition being administered one to four times per day. The rectal dose will be approximately the same as the oral dose.

The invention is illustrated, but not limited, by the following examples in which the temperatures are in degrees Centigrade and the following abbreviations are used: DMF (dimethyl formamide), EtOAc (ethyl acetate), MeOH (methanol), EtOH (ethanol), ether (diethyl ether). THF (tetrahydrofuran), g. (grams), ml. (milliliter), w. (weight), v. (volume), M (molar), N (normal), HPLC (high pressure liquid chromatography), m.p. (melting point). The chemical symbols have their usual meanings unless otherwise indicated.

EXAMPLE 1

4-Amino-6,7-dihydro-1-(pent-3-ynyl)-6-n-propyl-pyrazolo[3,4-b]pyrrolo[3,4-e]pyridin-5(1H)-one
(Formula II, Ra=pent-3-ynyl, Rb=H, Rc=n-propyl, n=1)

A suspension of 4-amino-6,7-dihydro-1H-6-n-propyl-pyrazolo[3,4-b]pyrrolo[3,4-e]pyridin-5(1H)-one (8.0 g.) and finely ground anhydrous potassium carbonate (14.34 g.) in dry DMF (100 ml.) was stirred at room temperature while 1-bromo-3-pentyne (8.34 ml.) was added. The mixture was stirred under nitrogen for two days, after which additional portions of potassium carbonate (5.0 g.) and 1-bromo-3-pentyne (2.1 ml.) were added. After one more day of stirring under nitrogen, the mixture was poured into water (300 ml) and the product extracted into EtOAc. The extract was washed with brine, dried ($Na_2SO_4$), and evaporated to give a light yellow solid. The solid was triturated with hexane, and the hexane discarded. The remaining solid was dissolved in EtOAc containing a small volume of MeOH and was chromatographed over flash silica gel (400 g.) using EtOAc/hexane (1:1 v/v) as the eluant. The resulting solid was recrystallized from toluene (200 ml.) to give 6.84 g. of the title compound, m.p. 178°–179.5°. A second recrystallization from toluene provided an analytical sample, m.p. 178.5–179.5°.

Calculated for $C_{16}H_{19}N_5O$: C, 64.63: H, 6.44; N, 23.55 Found: C, 64.81: H, 6.27: N, 23.35

The starting material was obtained as follows:

(i) A solution of 2-hydroxyethylhydrazine (38.9 g.) in EtOH (425 ml.) was heated to 50° while a solution of ethoxymethylenemalononitrile (52 g.) in warm EtOH (250 ml.) was added over a period of ten minutes. The last of this material was washed into the reaction flask with EtOH (50 ml.), and the mixture was heated under reflux for 2.5 hours. The resulting solution was allowed to cool to room temperature overnight. The golden-brown crystals which formed were collected by filtration, washed with ether, and dried in vacuo at room temperature to give 5-amino-4-cyano-1-(2-hydroxyethyl)pyrazole (45.57 g.): m.p. 158°–160 °.

(ii) A suspension of 5-amino-4-cyano-1-(2hydroxyethyl)pyrazole (40 g.) and triphenylphosphine (82.7 g.) in dichloromethane (300 ml.) was cooled in a room temperature water bath while carbon tetrachloride (127 ml.) was added dropwise over 45 minutes. The resulting suspension was stirred at room temperature under nitrogen overnight, and the volatiles were then removed on a rotary evaporator, leaving an orange semisolid. This was treated with boiling EtOAc (500 ml.), chilled at 0°, filtered, and the filtrate evaporated to dryness. The residue was redissolved in THF (300 ml.) and evaporated onto flash silica gel (160 g.). This material was placed atop a column of flash silica gel (300 g.) and the desired product eluted with EtOAc/hexane (1:1 v/v). Contaminating triphenylphosphine oxide was removed by trituration with dichloromethane/hexane (1:1 v/v). The remaining solid was then recrystallized from EtOAc to give 5-amino-1-(2-chloroethyl)-4-cyanopyrazole (29.07 g.) as white crystals: m.p. 155.5–156.5 °.

(iii) A solution of n-propylamine (325 g.) in diethyl ether (1500 ml.) was cooled to 0° with stirring while a solution of ethyl bromoacetate (459 g.) in diethyl ether (500 ml.) was added over 50 minutes. The reaction was then stirred for 2 hours at 0° and for 2 hours at room temperature, at which point the mixture was filtered, and the filter cake washed thoroughly with diethyl ether. The filtrate was evaporated to afford a crude product which was purified by distillation. That fraction boiling within the range of 69°–90° at 11 mm Hg (11 Torr, 1466.54 Pascals) was collected, providing 291.9 g. (73% yield) of ethyl N-(n-propyl)glycinate.

(iv) A mixture of $K_2CO_3$ (277 g.), water (1000 ml.), diethyl ether (2000 ml.), and THF (200 ml.) was cooled to 5° with stirring. To this mixture was added, from separate dropping funnels, ethyl N-(n-propyl)glycinate (290 g.) and ethyl malonyl chloride (316 g.) over a period of 1.5 hours. After completion of the addition, the mixture was stirred at 5° for 1 hour, then allowed to warm to room temperature overnight with stirring. At this time another portion of ethyl malonyl chloride (25 g.) was added, and the mixture was stirred another 30 minutes at room temperature. The layers were separated, and the aqueous phase was extracted with diethyl ether (700 ml.). The combined organic phases were washed with water (1000 ml.) and dried (MgSO$_4$). Evaporation provided 503.6 g. (97% yield) of ethyl N-(ethoxycarbonylacetyl)-N-(n-propyl)glycinate as a pale yellow oil.

(v) To absolute ethanol (1800 ml.) was added metallic sodium (43.8 g.) and the mixture was stirred under nitrogen until dissolution was complete. The resulting solution was maintained at 30° while a solution of ethyl N-(ethoxycarbonylacetyl)-N-(n-propyl)glycinate (503.5 g.) in toluene (4000 ml.) was added over a period of 1.5 hours. The mixture was then heated to reflux for 5 hours, then cooled and allowed to stir at room temperature overnight. To the mixture was added cold water (3000 ml.) and the resulting mixture was stirred for 30 minutes. The phases were separated, and the organic phase was extracted once with water (500 ml.) and then discarded. The combined aqueous phases were acidified to pH 1 by the dropwise addition of concentrated hydrochloric acid (200 ml.). The resulting aqueous suspension of product was extracted four times with dichloromethane (700 ml. each), and the combined organic extracts were dried (Na$_2$SO$_4$). Evaporation at reduced pressure provided a crude product which was purified by repeated trituration with diethyl ether. The resulting solid was dried in vacuo at 40° to provide 333.9 g. (81% yield) of 1-(n-propyl)-3-ethoxycarbonyl-pyrrolidin-2,4-dione as a white powder: m.p. 123°–125 °.

(vi) A solution of 1-(n-propyl)-3-ethoxycarbonylpyrrolidin-2,4-dione (21.6 g.) in acetonitrile (400 ml.) containing water (12 ml.) was heated under reflux for 30 minutes. The solvents were then removed under reduced pressure (bath temperature 45° ) leaving a brown oil. This was immediately redissolved in toluene (500 ml.). 5-Amino-1-(2-chloroethyl)-4-cyanopyrazole (11.5 g.) and a catalytic amount of toluene-p-sulfonic acid monohydrate (0.35 g.) were then added, and the mixture was heated under reflux with removal of water in a Dean-Stark trap. After 5.5 hours, the mixture was cooled to room temperature with vigorous stirring, and was then allowed to stand at −20° overnight. The white crystals which formed were collected by filtration, washed with toluene and hexane in succession, and dried in vacuo at room temperature. This gave 18.22 g. of 5-[N-(n-propyl)2-oxo-3-pyrrolin-4-yl]amino-1-(2-chloroethyl)-4-cyanopyrazole: m.p. 181.5°–184.5 °.

(vii) A suspension of 5-[N-(n-propyl)-2-oxo-3-pyrrolin-4-yl]amino-1-(2-chloroethyl)-4-cyanopyrazole (18.22 g.) in dry dichloromethane (218 ml.) was cooled at 0° under nitrogen with stirring, while a solution of trimethylaluminum in heptane (92 ml. of 1.35 M solution) was added dropwise. Gas evolved. The resulting clear yellow solution was warmed to room temperature and allowed to stir under nitrogen overnight. After cooling to 0° and introducing a vigorous stream of nitrogen, 3N aqueous HCl was added cautiously until gas evolution ceased. The mixture was then diluted with EtOAc (200 ml.) and water (200 ml.), and the precipitated aluminum salts were solubilized by treatment with a 10% w/v solution of sodium hydroxide in water. The product was extracted into EtOAc. This extract was washed with 10% sodium hydroxide and brine in succession, and then dried (Na$_2$SO$_4$). Evaporation gave a white solid which was recrystallized from a minimum of EtOAc to give 16.44 g. of 4-amino-1(2-chloroethyl)-6,7-dihydro-6-n-propylpyrazolo[3,4-b]-pyrrolo[3,4-e]pyridin-5(1H)-one as white crystals: m.p. 195.5°–196.5 °.

(viii) A solution of 4-amino-1-(2-chloroethyl)-6,7-dihydro-6-n-propylpyrazolo[3.4-b]pyrrolo[3,4-e]pyridin-5(1H)-one (16.44 g.) in dry DMF (65 ml.) was treated with 1,8-diazabicyclo[5.4.0]undec-7-ene (16.8 ml.). The mixture was heated to 100° under nitrogen with stirring for 3 hours. After cooling, the mixture was poured into water (600 ml.) and the product was extracted into EtOAc. The extract was washed with water, then brine, and evaporated to leave a white solid which was recrystallized from acetonitrile. There was thus obtained 11.67 g. of 4-amino 6,7-dihydro-6-(n-propyl)-1-vinylpyrazolo[3,4-b]pyrrolo[3,4-e]pyridin-5-(1H)-one as white crystals. Recrystallization from EtOAc gave a sample: m.p. 185°–185.5 °.

(ix) A mixture of 4-amino-6,7-dihydro-6-(n-propyl)-1-vinylpyrazolo[3,4-b]pyrrolo[3,4-e]pyridin5-(1H)-one (9.9 g.) and acetonitrile (250 ml.) was stirred while 6N aqueous hydrochloric acid (100 ml.) was added. The mixture was heated under reflux for 3.5 hours under nitrogen. The cooled suspension was neutralized by the cautious addition of saturated aqueous sodium carbonate and the acetonitrile was removed at reduced pressure. The aqueous suspension of product was chilled to 4° overnight. The precipitated white solid was collected by filtration, washed with water, and dried in vacuo. There was thus obtained 8.0 g. of 4-amino-6,7-dihydro-1H-6-n-propylpyrazolo[3,4-b]pyrrolo[3,4-e]pyridin-5-(1H)-one. Recrystallization from acetonitrile gave a sample: m.p. 278°–281 °.

EXAMPLE 2

4-Amino-6,7-dihydro-1-(hex-4-ynyl)-6-n-propyl-pyrazolo[3,4-b]pyrrolo[3,4-e]pyridin-5(1H)-one (Formula II, Ra=hex-4-ynyl, Rb=H, Rc=n-propyl, n=1).

The process described in Example 1 was repeated using 1-iodo-4-hexyne in place of 1-bromo-3-pentyne. There was thus obtained the title compound in 41% yield, m.p. 168°–169.5°.

Calculated for C$_{17}$H$_{21}$N$_5$O: C, 65.57: H, 6.80: N, 22.49

Found: C, 65.41: H, 6.73: N, 22.24

EXAMPLE 3

4-Amino-6-(n-butyl)-6,7-dihydro-1-(pent-3-ynyl)-pyrazolo[3,4-b]pyrrolo[3,4-e]pyridin-5(1H)-one (Formula II, Ra=pent-3-ynyl, Rb=H, Rc=n-butyl, n=1).

To a solution of 5-[N-(n-butyl)-2-oxo-3-pyrrolin-4-yl]amino-1-(pent-3-ynyl)-4-cyanopyrazole (0.88 g.) in dry dichloromethane (20 ml.) was added a solution of trimethylaluminium in heptane (4.2 ml. of a 1.35 M solution) while stirring at room temperature under nitrogen. After stirring overnight, the reaction was quenched by the cautious addition of 3N aqueous hydrochloric acid until gas evolution had ceased. The precipitated aluminium salts were solubilized by addition of a 10% w/v aqueous solution of sodium hydroxide and the product was extracted into EtOAc. The extract was washed with 10% w/v aqueous sodium hydroxide solution and then brine, dried (Na$_2$SO$_4$), and evaporated to leave a light yellow solid. Recrystallization from toluene/hexane gave the title compound as a white crystalline powder (0.5 g.): m.p. 171°–172.5°.

Calculated for $C_{17}H_{21}N_5O$: C, 65.57: H, 6.80; N, 22.49 Found: C, 65.48: H, 6.94: N, 22.72

The starting material may be obtained as follows:

(i) To a suspension of 5-amino-4-cyanopyrazole (15 g.) and finely ground potassium carbonate (58 g.) in dry DMF (100 ml.) was added 1-bromo-3-pentyne (24.5 g). After stirring at room temperature under nitrogen for 2 days, additional portions of potassium carbonate (10 g.) and 1-bromo-3-pentyne (5 g.) were added. After three more days of stirring, a final portion of 1-bromo-3-pentyne (5 g.) was added, and the reaction allowed to proceed two more days. At this time the reaction mixture was poured into water and the product extracted into EtOAc. The extract was washed with brine, dried ($Na_2SO_4$), and evaporated to an oil which was subjected to preliminary purification on a column of flash silica gel. Elution with hexane/ EtOAc (2:1 v/v) gave a mixture of the isomeric compounds 5-amino-4-cyano-1-(pent-3-ynyl)pyrazole and 3-amino-4-cyano-1-(pent-3-ynyl)-pyrazole. This mixture was separated by preparative HPLC on silica gel, using hexane/EtOAc (1:1 v/v) as eluant. After pooling appropriate fractions, recrystallization from EtOAc/ hexane gave 5.05 g. of the desired 5-amino-4-cyano-1-(pent-3-ynyl)-pyrazole: m.p. 116.5°–117°.

(ii) 1-(n-Butyl)-3-ethoxycarbonylpyrrolidin2,4-dione, m.p. 121°–123°, was obtained as described for 1-(n-propyl)-3-ethoxycarbonylpyrrolidin-2,4-dione in Example 1, but substituting n-butylamine for n-propylamine in the preparation of ethyl N-(n-propyl)glycinate. The resulting ethyl N-(n-butyl)glycinate was then reacted with ethyl malonyl chloride as described in Example 1 in the preparation of ethyl N-(ethoxycarbonylacetyl)-N-(n-propyl)glycinate. The resulting ethyl N-(ethoxycarbonylacetyl)-N-(n-butyl)glycinate was transformed into 1-(n-butyl)-3-ethoxycarbonylpyrrolidin-2,4-dione by reaction with a solution of sodium in ethanol as described in Example 1.

(iii) A solution of 1-(n-butyl)-3-ethoxycarbonyl-pyrrolidin-2,4-dione (1.02 g.) in wet acetonitrile (23 ml.) was heated under reflux for 1.5 hours. The acetonitrile was evaporated under reduced pressure, leaving a clear oil which was immediately dissolved in toluene (28 ml.). To this solution was added 5-amino-1-(pent-3-ynyl)-4-cyanopyrazole (0.6 g.) and a catalytic amount of toluene-p-sulphonic acid (0.05 g.). The mixture was heated under reflux overnight, collecting water in a Dean-Stark trap. The reaction mixture was cooled to 0° and diluted with ether. The resulting precipitate was collected by filtration, giving 0.89 g. of 5-[N-(n-butyl)-2-oxo-3-pyrrolin-4-yl]amino-1-(pent-3-ynyl)-4-cyanopyrazole, which was used without further purification.

EXAMPLE 4

4-Amino-7,8-dihydro-1-(pent-3-ynyl)-6-(prop-2-ynyl)-1H-pyrazolo-[3,4-b][1,6]naphthyridin-5(6H)-one
(Formula II, Ra=pent-3-ynyl, Rb=H, Rc=prop-2-ynyl, n=2).

To a suspension of powdered anhydrous potassium carbonate (2.41 g.) in dry DMF (15 ml.) under a nitrogen atmosphere at room temperature was added 4-amino-7,8-dihydro-6-(prop-2-ynyl)-1H-pyrazoloadded [3,4-b][1,6]napthyridin-5(6H)-one (0.84 g.) in dry DMF (5 ml.). After stirring five minutes, 1-bromo-3pentyne (0.61 g.) was added, followed by heating to 50° for two hours. An additional 0.5 equivalent of 1-bromo-3-pentyne (0.61 g.) was added, followed by heating to 50° for two hours. An additional 0.5 equivalent of 1-bromo-3-pentyne (0.3 g.) was added. The reaction mixture was then stirred at room ter:perature overnight (17 hours). Water (10 ml.) was added with subsequent extraction into EtOAc (3×10 ml.). The combined extracts were washed with brine, dried over magnesium sulfate, filtered through diatomaceous earth and concentrated to give a yellow-brown oil. Chromatography using silica gel using acetone/methylene chloride (1:1 v/v) as eluant afforded an off-white solid, which was recrystallized from t-butyl methyl ether to give a white powder (0.32 g.) (30% yield): m.p. 196°–197.5°.

Calculated for $C_{17}H_{17}N_5O$: C, 66.43: H, 5.57: N, 22.79 Found: C, 66.42: H, 5.67: N, 22.26

The starting material was obtained as follows:

(i) A stirred solution of 5-amino-1-(2-chloroethyl)-4-cyanopyrazole (1Z.0 g.), Z,4-dioxopiperidine (7.96 g.) and catalytic toluene-p-sulfonic acid monohydrate in dry toluene under a nitrogen atmosphere was placed in a 130° preheated oil bath with removal of the toluene/water azeotrope in a Dean-Stark trap. After four hours, the remaining toluene was removed by distillation. The residue was cooled to room temperature, taken up in EtOAc, and washed sequentially with aqueous saturated sodium carbonate and brine. The yellow organic layer was dried over magnesium sulfate, filtered through diatomaceous earth and concentrated to leave a brownish oil. Column chromatography using silica gel with acetone/methylene chloride (1:1 v/v) as eluant gave 5-[N-(2-oxo-1,2,5,6-tetrahydropyridin-4-yl)]amino-1-(2-chloroethyl)-4-cyanopyrazole as a white solid, which was recrystallized from acetonitrile giving a white powder (12.31 g.), (66% yield).

(ii) To a mechanically stirred suspension of 5-[N-(2-oxo-1,2,5,6-tetrahydropyridin-4-yl)]amino-1-(2-chloroethyl)-4-cyanopyrazole (12.31 g.) in dry methylene chloride (100 ml.) under a nitrogen atmosphere at 0° was added slowly trimethylaluminum (68.64 ml. of a 1.35 M solution in heptane). There was a vigorous gas evolution. The resulting yellowish sludge was warmed to room temperature and stirred for one hour. EtOAc was added, the yellow solution was cooled to 0° , and enough 10% v/v aqueous hydrochloric acid was cautiously added to bring the pH to 4 (about 15 ml.). The reaction mixture was stirred overnight (17 hours). 10% w/v Aqueous sodium hydroxide solution (500 ml.) was added and the mixture stirred for three hours, followed by extraction several times into EtOAc/MeOH (9:1 v/v). The extracts were washed with brine, dried over magnesium sulfate, filtered through diatomaceous earth and concentrated to an off-white solid. Chromatography using silica gel with acetone/ methylene chloride (1:1 v/v) as eluant gave 4-amino-1-(2-chloroethyl)-7,8-dihydro-1H-pyrazolo[3,4-b][1,6]-napthyridin -5(6H)-one as a white solid (8.89 g.) (72% yield).

(iii) To sodium hydride previously washed with distilled THF (1.75 g. of a 55% w/w oil dispersion) in dry acetonitrile (150 ml.) under a nitrogen atmosphere was added solid 4-amino-1-(2-chloroethyl)-7,8-dihydro-1H-pyrazolo[3,4-b][1,6]napthyridin-5(6H)-one (8.89 g.) in several portions. The reaction mixture was heated under reflux for three hours, cooled to room temperature and diluted with water. The reaction mixture was then extracted into EtOAc, then the extract was dried over magnesium sulfate, filtered through diatomaceous earth and concentrated to an off-white solid. Column chromatography using silica gel with acetone/methylene chloride (1:1 v/v) as eluant gave 4-amino-7,8-dihydro-1-vinyl-1H-pyrazolo[3,4-b][1,6]napthyridin-5(6H)-one as a white solid (7.09 g.), (92% yield).

(iv) To sodium hydride previously washed with distilled THF (0.52 g. of a 55% w/w oil dispersion) in freshly distilled dry THF (15 ml.) under a nitrogen atmosphere was added solid 4-amino-7,8-dihydro-1-vinyl-1H-pyrazolo[3,4-b][1,6]napthyridin-5-(6H)-one (Z.5 g.) in several portions over five minutes. The resulting yellow suspension was stirred at 45° for thirty minutes. The yellow solution was cooled to room temperature, followed by the addition of 1-bromo-2-propyne (1.87 ml.). After stirring two hours, water was added. The reaction mixture was extracted into EtOAc, the extract washed with brine, dried over magnesium sulfate, filtered through diatomaceous earth and concentrated to a yellow-brown oil. Chromatography on silica gel using EtOAc/hexane (1:1 v/v) as eluant gave 4-amino-7,8-dihydro-6-(prop-2-ynyl)-1-vinyl-1H-pyrazolo[3,4-b][1,6]napthyridin-5(6H)-one as a yellow solid (1.91 g.), (65% yield).

(v) To a mechanically stirred solution of 4-amino-7,8-dihydro-6-(prop-2-ynyl)-1-vinyl-1H-pyrazolo[3,4-b][1,6]napthyridin-5(6H)-one (1.91 g.) in dry acetonitrile (35 ml.) under a nitrogen atmosphere was added freshly prepared 6N aqueous HCl (11.65 ml.) at room temperature. The resulting suspension was heated under reflux for three hours, followed by cooling to room temperature and addition of water. The reaction mixture was made basic with aqueous saturated sodium carbonate and extracted with EtOAc. The organic phase was washed with brine, dried over magnesium sulfate, filtered through diatomaceous earth and concentrated to give 4-amino-7,8-dihydro-6-(prop-2-ynyl)-1H-pyrazolo[3,4-b][1,6]napthyridin-5(6H)-one as a white solid (1.24 g.) (72% yield) which was used without further purification.

EXAMPLE 5

4-(n-Butyramido)-6,7-dihydro-1-(pent-3-ynyl)-6-n-propylpyrazolo[3,4-b]pyrrolo[3,4-e]pyridin-5(1H)-one
(Formula II, Ra=pent-3-ynyl, Rb=n-butyryl, Rc=n-propyl, n=1)

A mixture of the product of Example 1 (0.7 g.) and 4-dimethylaminopyridine (0.32 g.) in dry toluene (15 ml.) was treated with n-butyric anhydride (3.84 ml.) under nitrogen at room temperature. The mixture was heated under reflux overnight and then cooled to room temperature. The toluene was evaporated in a stream of nitrogen and the residue was dissolved in ether (10 ml.). This ethereal solution was treated with water (10 ml.), and then with sodium bicarbonate, which was added in portions over several hours until the excess of butyric anhydride had been hydrolyzed. The product was extracted into ether, and the extract was washed with brine and dried ($Na_2SO_4$). Evaporation left a white solid which was dissolved in a small volume of EtOAc and chromatographed over flash silica gel. Elution with hexane/EtOAc (2:1 v/v) gave a white solid which was recrystallized from ether/hexane to give 0.67 g. of the title compound as slightly yellowish-white crystals; m.p. 116°–117°.

Calculated for $C_{20}H_{25}N_5O_2$: C, 65.37: H, 6.86: N, 19.06 Found: C, 65.51: H, 6.92: N, 19.18

EXAMPLE 6

4-(n-Valeramido)-6,7-dihydro-1-(pent-3-ynyl)-6-n-propylpyrazolo[3,4-b]pyrrolo[3,4-e]pyridin-5(1H)-one
(Formula II, Ra=pent-3-ynyl, Rb=n-valeryl, Rc=npropyl, n=1)

The procedure of Example 5 was followed, substituting n-valeric anhydride for n-butyric anhydride. The title compound was obtained in 67% yield as white crystals from ether/hexane: m.p. 113.5°–114.5°.

Calculated for $C_{21}H_{27}N_5O_2$: C, 66.12: H, 7.13: N, 18.36 Found: C, 66.20: H, 7.24: N, 18.52

EXAMPLE 7

4-Acetamido-6,7-dihydro-1-(pent-3-ynyl)-6-n-propyl-pyrazolo[3,4-b]pyrrolo[3,4-e]pyridin-5(1H)-one
(Formula II, Ra=pent-3-ynyl, Rb=acetyl, Rc=n-propyl, n=1)

The procedure of Example 5 was followed, substituting acetic anhydride for n-butyric anhydride. The title compound was obtained in 35% yield as white crystals from ether: m.p. 132°–133°.

Calculated for $C_{18}H_{21}N_5O_2$: C, 63.70: H, 6.23: N, 20.63 Found: C, 63.97: H, 6.37: N, 20.50

EXAMPLE 8

4-Propionamido-6,7-dihydro-1-(pent-3-ynyl)-6-n-propylpyrazolo[3,4-b]pyrrolo[3,4-e]pyridin-5(1H)-one
(Formula II, Ra=pent-3-ynyl, Rb=propionyl, Rc=npropyl, n=1)

The procedure of Example 5 was followed, substituting propionic anhydride for n-butyric anhydride. The title compound was obtained in 50% yield as white crystals from ethyl acetate/hexane: m.p. 130.5°–132°.

Calculated for $C_{19}H_{23}N_5O_2$: C, 64.57: H, 6.56; N, 19.82 Found: C, 64.46: H, 6.52: N, 19.64

EXAMPLE 9

4-(n-Hexanoamido)-6,7-dihydro-1-(pent-3-ynyl)-6-n-propylpyrazolo[3,4-b]pyrrolo[3,4-e]pyridin-5(1H)-one
(Formula II, Ra=pent-3-ynyl, Rb=n-hexanoyl, Rc=n-propyl, n=1)

The procedure of Example 5 was followed, substituting n-hexanoic anhydride for n-butyric anhydride. The title compound was obtained in 61% yield as white crystals from ether/hexane: m.p. 98°–99°.

Calculated for $C_{22}H_{29}N_5O_2$: C, 66.81: H, 7.39; N, 17.71
Found: C, 66.85: H, 7.46: N, 17.55

EXAMPLE 10

4-Amino-6,7-dihydro-1-(pent-3-ynyl)-6-(2-propenyl)-pyrazolo[3,4-b]pyrrolo[3,4-e]pyridin-5(1H)-one
(Formula II, Ra=pent-3-ynyl, Rb=H, Rc=2-propenyl, n=1)

A suspension of 4-amino-6,7-dihydro-1H-6-(2-propenyl)pyrazolo[3,4-b]pyrrolo[3,4-e]pyridin-5(1H)-one (1.5 g.) and finely ground anhydrous potassium carbonate (2.71 g.) in dry DMF (37.5 ml.) was stirred at room temperature while 1-bromo-3-pentyne (1.5 ml.) was added. The mixture was stirred under nitrogen for one day, after which additional portions of potassium carbonate (1.81 g.) and 1-brom-o-3-pentyne (0.75 ml.) were added. After three more days of stirring under nitrogen, the mixture was poured into water (50 ml.) and the product extracted into EtOAc. The extract was washed with brine, dried (Na₂SO₄), and evaporated to give a yellow solid. This was dissolved in EtOAc containing a small volume of MeOH and was chromatographed over flash silica gel (100 g.) using EtOAc/hexane (1:1 v/v) as the eluant. The resulting solid was recrystallized from toluene (120 ml.) to give 1.26 g. of the title compound: m.p. 192.5°–193.5°.

Calculated for C₁₆H₁₇N₅O: C, 65.07; H, 5.80: N, 23.71 Found: C, 64.90: H, 5.83: N, 23.34

The starting material was obtained as follows:

(i) 1-(2-Propenyl)-3-ethoxycarbonylpyrrolidin-2,4-dione, m.p. 143°–146°, was prepared as described for 1-(n-propyl)-3-ethoxycarbonylpyrrolidin-2,4-dione in Example 1, but substituting 2-propenylamine for n-propylamine. The resulting ethyl N-(2-propenyl)glycinate was then reacted with ethyl malonyl chloride as described in Example 1 in the preparation of ethyl N-(ethoxycarbonylacetyl)-N-(n-propyl)glycinate. The resulting ethyl N-(ethoxycarbonylacetyl)-N-(2-propenyl)-glycinate was then transformed into 1-(2-propenyl)-3-ethoxycarbonylpyrrolidin-2,4-dione by reaction with a solution of sodium in ethanol as described in Example 1.

(ii) A solution of 1-(2-propenyl)-3-ethoxy-carbonyl-pyrrolidin-2,4-dione (19.93 g.) in acetonitrile (400 ml.) containing water (12 ml.) was heated to reflux for 5 minutes, during which time gas was evolved. There was then added 5-amino-1-(2-chloro ethyl)-4-cyanopyrazole (11.5 g. prepared as in Example 1) and toluene-p-sulfonic acid monohydrate (0.35 g.). The mixture was again heated to reflux, distilling out solvent while adding toluene to keep the volume of the reaction mixture constant. This procedure was applied for 1 hour, during which time the boiling point of the distillate rose to 111°, and 1 liter of distillate had been collected. The distillation head was then fitted with a Dean-Stark trap, and the reflux was continued with removal of water. After 2½ hours the mixture was cooled to room temperature with vigorous stirring, and was then cooled to 0°. The off-white crystals which formed were collected by filtration, washed with toluene and hexane in succession, and dried in vacuo at room temperature. This gave 19.14 g. of 5-[N-(2-propenyl)-2-oxo-3-pyrrolin-4-yl]amino-1-(2-chloroethyl)-4-cyanopyrazole: m.p. 174°–176°.

(iii) A suspension of 5-[N-(2-propenyl)-2-oxo-3-pyrrolin-4-yl]amino-1-(2-chloroethyl)-4-cyanopyrazole (19.60 g.) in dry dichloromethane (200 ml.) was cooled to 0° under nitrogen with stirring, while a solution of trimethylaluminium in hexane (57 ml. of 25 wt. % solution) was added dropwise. Gas evolved. The resulting clear yellow solution was warmed to room temperature and allowed to stir under nitrogen for three days. After cooling to 0° and introducing a vigorous stream of nitrogen, 3N aqueous HCl was added cautiously until gas evolution ceased. The mixture was then diluted with aqueous NaOH (400 ml. of 20% w/v solution) and dichloromethane (500 ml.) and the phases were separated. The aqueous layer was further extracted twice with dichloromethane (250 ml. each time) and the organic extracts were combined. These were washed with aqueous NaOH (250 ml. of 10% w/v solution), and then with brine (400 ml.), and finally dried (Na₂SO₄) Evaporation gave a yellow solid which was recrystallized from a minimum of EtOAc to give 4-amino-1-(2-chloroethyl)-6,7-dihydro-6-(2-propenyl)pyrazolo[3,4-b]pyrrolo[3,4-e]pyridin-5(1H)-one as a light yellow powder, 15.71 g.: m.p. 197.5°–199°.

(iv) A solution of 4-amino-1-(2-chloroethyl)-6,7-dihydro-6-(2-propenyl)pyrazolo[3,4-b]pyrrolo[3,4-e]pyridin-5(1H)-one (15.69 g.) in dry DMF (65 ml.) was treated with 1,8-diazabicyclo[5.4.0]undec-7-ene (9.65 ml.). The mixture was heated to 110° under nitrogen with stirring for five hours. After cooling, the mixture was poured into water (400 ml.) and the product was extracted into dichloromethane. The extract was washed with brine, dried (Na₂SO₄) and evaporated at reduced pressure to afford a suspension of crude product in DMF. This was warmed to effect complete dissolution, and water (350 ml.) was added to precipitate the product. After cooling to 0°, the precipitated solid was collected by filtration, washed with water, and dried in vacuo at 50°. In this manner there was obtained 11.09 grams of 4-amino-6,7-dihydro6-(2-propenyl)-1-vinyl-pyrazolo[3,4-b]pyrrolo[3,4-e]pyridin-5(1H)-one as a light yellow solid: m.p. 190°–191°.

(v) A mixture of 4-amino-6,7-dihydro-6-(2-propenyl)-1-vinylpyrazolo[3,4-b]pyrrolo[3,4-e]pyridin5(1H)-one (11.09 g.) and acetonitrile (350 ml.) was heated to reflux under nitrogen. To the rapidly stirred solution was added 6N aqueous hydrochloric acid (76 ml.) and acetonitrile (50 ml.) and the reflux was continued for two hours. After cooling to 45°, there was added an aqueous solution of NaOH (92 ml. of 20% w/v solution). The mixture was concentrated at reduced pressure, collecting 375 ml. of distillate, and the resulting aqueous suspension was chilled to 0°. The precipitated product was collected by filtration and washed with water, then dried in vacuo at 45°. In this manner there was obtained 9.02 grams of 4-amino-6,7-dihydro-1H-6-(2-propenyl)-pyrazo-lo[3,4-b]pyrrolo[3,4-e]pyridin-5(1H)-one as an offwhite powder: m.p. 265° (with decomposition).

EXAMPLE 11

4-Amino-6,7-dihydro-1-(hex-4-ynyl)-6-(2-propenyl)-pyrazolo[3,4-b]pyrrolo[3,4-e]pyridin-5(1H)-one
(Formula II, Ra=hex-4-ynyl, Rb=H, Rc=2-propenyl, n=1)

The process described in Example 10 was repeated using 1-iodo-4-hexyne in place of 1-bromo-3-pentyne. The title compound was thus obtained in 75% yield as white crystals from toluene/hexane: m.p. 137.5°–140.5°.

Calculated for C₁₇H₁₉N₅O: C, 66.00: H, 6.19: N, 22.64 Found: C, 65.60: H, 6.18: N, 22.47

What is claimed is:

1. A compound of formula II as follows:

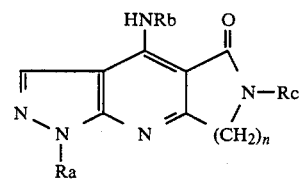

wherein
Ra is pent-3-ynyl or hex-4-ynyl:
Rb is hydrogen or (1-10C)alkanoyl:
Rc is (1-6C)alkyl, (3-6C)alkenyl, or (3-6C)alkynyl: and
n is 1 or 2: and the pharmaceutically-acceptable acid-addition salts thereof.

2. A compound according to claim 1.wherein Rb is selected from the group consisting of acetyl, propionyl, butyryl, valeryl and hexanoyl; Rc is selected from the group consisting of ethyl, n-propyl, n-butyl, 2-propenyl, 2-propynyl and 2-butynyl.

3. A compound according to claim 1 wherein said acid-addition salt is one formed with hydrochloric, hydrobromic, sulfuric, nitric or phosphoric acid.

4. A compound according to claim 1 wherein said compound is selected from the group consisting of a compound of formula II wherein:
(a) Ra is pent-3-ynyl, Rb is hydrogen, Rc is n-propyl, and n is one; (b) Ra is pent-3-ynyl, Rb is hydrogen, Rc is 2-propenyl, and n is one; and (c) Ra is pent-3-ynyl, Rb is propionyl, Rc is propyl, and n is one.

5. A pharmaceutical composition comprising a compound of claim 1 in an amount sufficient to affect anxioytic activity in a mammal in association wit a non-toxic pharmaceutically-acceptable diluent or carrier.

6. A method of relieving anxiety in a living mammal in need of such treatment which consists essentially of administering to said mammal an anti-anxiety effective amount of a compound of claim 1 in admixture with a pharmaceutically acceptable carrier.

* * * * *